United States Patent [19]

Suzaki et al.

[11] Patent Number: 4,652,916
[45] Date of Patent: Mar. 24, 1987

[54] IMAGE PICK-UP DEVICE

[75] Inventors: Takuji Suzaki, Uji; Koji Yamamoto, Kyoto, both of Japan

[73] Assignee: Omron Tateisi Electronics Co., Kyoto, Japan

[21] Appl. No.: 660,238

[22] Filed: Oct. 12, 1984

[30] Foreign Application Priority Data

Oct. 12, 1983 [JP] Japan .................. 58-190296

[51] Int. Cl.⁴ ............................... H04N 7/18
[52] U.S. Cl. ..................... 348/93; 358/211; 358/228; 358/213; 350/331 R
[58] Field of Search ............ 358/93, 228, 211, 901; 250/578; 350/509, 510, 523, 526, 331 R

[56] References Cited

U.S. PATENT DOCUMENTS

| | | | |
|---|---|---|---|
| 3,691,302 | 9/1972 | Gaebele et al. | 358/211 |
| 3,833,282 | 9/1974 | Kappl et al. | 250/528 X |
| 3,978,280 | 8/1976 | Kavanaugh et al. | 358/93 |
| 3,980,814 | 9/1976 | Crawley | 358/93 |
| 4,242,635 | 12/1980 | Burns | 350/331 R X |
| 4,300,107 | 11/1981 | Miller et al. | 358/228 X |
| 4,327,378 | 4/1982 | Tanaka et al. | 358/228 |
| 4,386,836 | 6/1983 | Aoki et al. | 350/331 R X |
| 4,423,436 | 12/1983 | Kimura | 358/211 X |
| 4,437,111 | 3/1984 | Inai et al. | 358/211 X |
| 4,516,032 | 5/1985 | Barr | 250/216 X |
| 4,561,731 | 12/1985 | Kley | 350/510 |

Primary Examiner—Howard W. Britton
Assistant Examiner—Victor R. Kostak
Attorney, Agent, or Firm—Stevens, Davis, Miller & Mosher

[57] ABSTRACT

An image pick-up device for picking up the image of an object having different degrees of brightness, ranging from a low degree to a high degree. The device includes a light source for irradiating the object, an image pick-up unit for picking up an image of the object, and an optical system disposed between the object and the image pick-up unit for forming the image of the object on the image pick-up unit. A discrimination circuit designates a region of high brightness in the image of the object picked-up by the image pick-up unit, and a detection circuit detects the brightness level of a designated region of high brightness. A light transmittance changing circuit reveives a representation of the detected brightness level of the designated region of high brightness from the detection circuit responsive to a designation of a region of high brightness by the discrimination circuit and decreases the light transmittance in a region of the optical system corresponding to the designated region of high brightness in the image. The discrimination circuit includes a comparison circuit for comparing the brightness of the image of the object with a predetermined reference level to automatically designate a region of high brightness.

4 Claims, 4 Drawing Figures

IMAGE PICK-UP DEVICE

BACKGROUND OF THE INVENTION

1. Field of the Invention

This invention relates to an image pick-up device, and particularly to improvements in an image pick-up device for picking up the image of an object having different degrees of brightness ranging from a low degree to a high degree.

2. Prior Art

Generally, an image pick-up device using an image pick-up tube or a solid-state image pick-up element is provided with an AGC (automatic gain control) circuit for preventing damage, such as seizure, or for obtaining an image with a suitable degree of brightness. In this connection, it is to be noted that depending upon the type of object being imaged, there may be a mixture of high and low degrees of brightness in the image. For example, when a biological organ is observed with reflected light from a light source, since the surface is wet, the image of the light source itself can be reflected from the surface of the organ, resulting in an image thereof being formed on the image pick-up tube or image pick-up element. In this case, the portion where the image of the light source is formed as a result of the reflected light is very high in brightness, while the other portion desired to be observed is dark. If, in such situation, the AGC circuit is operating, AGC will be applied more to the portion of high brightness, with the portion desired to be observed becoming much darker, thus making it difficult to attain minute observation.

On the other hand, if the AGC circuit is eliminated and instead the sensitivity (applied voltage) of the image pick-up device is increased, there arises a problem that the image pick-up element associated with the portion receiving a greater amount of incident light develops the so-called seizure phenomenon and is thereby damaged.

SUMMARY OF THE INVENTION

It is an object of the invention to provide an image pick-up device which ensures that even whens the image of an object having a mixture of high and low degrees of brightness is to be picked up, minute observation is attained by sufficiently increasing the brightness of the portion desired to be observed without causing said seizure.

In brief, this invention is directed to a device including light transmittance changing means which is associated with an optical system for forming the image of an object on an image pick-up means, the arrangement being such that the light transmittance in the region of the light transmittance changing means corresponding to the region of high brightness in the image of the object picked up by the image pick-up means is decreased.

According to this invention, since only the portion of high brightness in the image of the object picked up by the image pick-up means is designated and the brightness of said portion is decreased, it is possible in increase the sensitivity of the image pick-up device in the portion desired to be observed, without causing seizure to the image pick-up device.

This invention will now be described in more detail in conjunction with an embodiment thereof shown in the drawings.

DETAILED DESCRIPTION OF THE INVENTION

Figure 1:
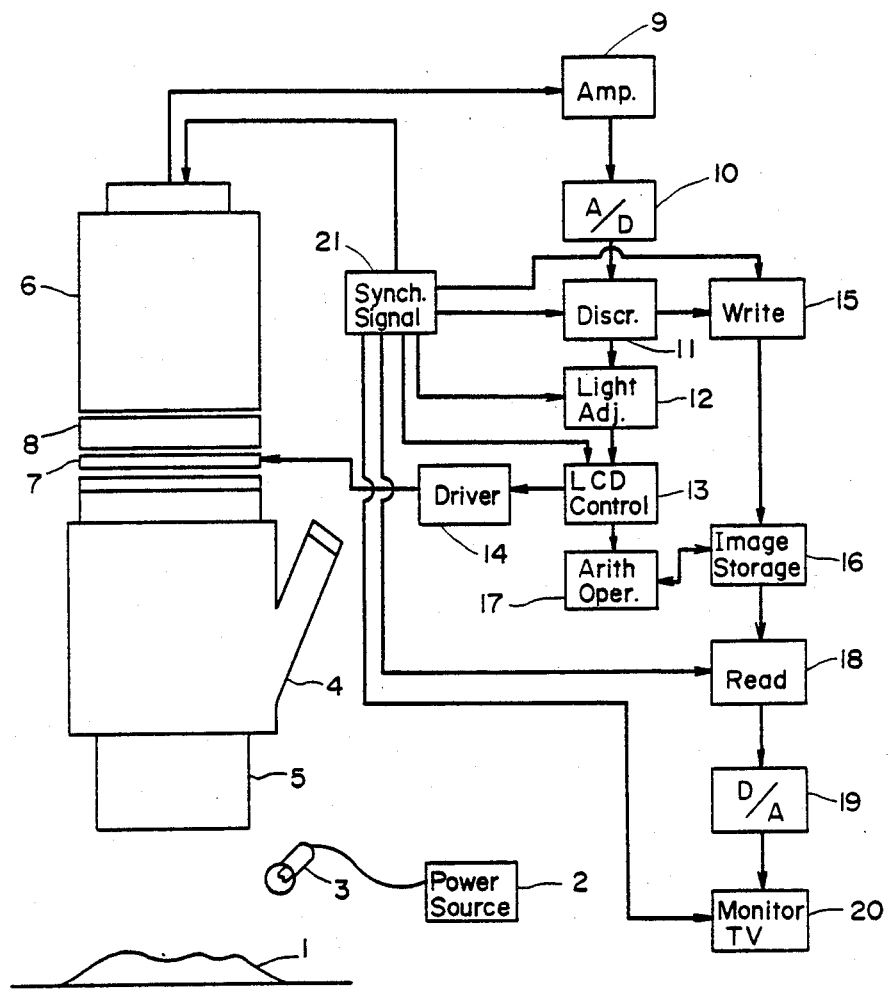
FIG. 1 is a block diagram schematically showing an embodiment of this invention.
Figure 4:
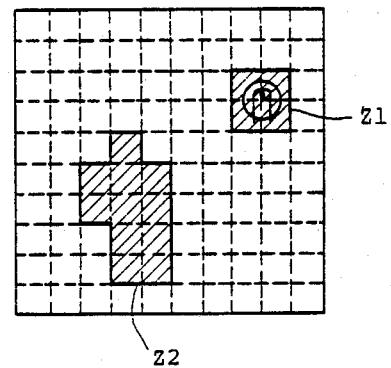
FIG. 4 is a view showing the state of the liquid crystal element 7 during correction.

FIG. 1 is a block diagram schematically showing an embodiment of this invention. In this figure, a biological organ 1 (hereinafter referred to as the organ), which is an example of an object to be photographed, is irradiated with illuminating light from above by an illuminator or light source 3 having a power source unit 2. The reflected light from the organ 1 is condensed by an objective lens 5 and magnified by a microscope 4. The image magnified by the microscope 4 is passed through an optical fiber 8 to an image pick-up tube 6, which is an example of an image pick-up means. In addition, a liquid crystal element 7 is disposed on the image forming surface of the microscope 4. Thus, the optical fiber 8 transmits the image which has passed through the liquid crystal element 7 to the image pick-up tube 6. In addition, the image pick-up tube 6 may be replaced by a solid-state image pick-up element. Further, the optical fiber 8 may be replaced by a lens system. The liquid crystal element 7, as shown in FIG. 4 to be described in detail below, is partitioned into a plurality of regions, and the light transmittance of each region can be changed.

The output from the image pick-up tube 6 is fed to an amplifying circuit 9. The amplifying circuit 9 is so arranged that its amplification factor can be manually changed from the outside. The output from the amplifying circuit 9 is fed to an A/D conversion circuit 10, and the analog picture element signal is converted into a digital signal. The output from the A/D conversion circuit 10 is fed to a discriminating circuit 11. The discriminating circuit 11 is a circuit for determining whether or not the level (brightness) of the picture element signal from the A/D conversion circuit 10 is higher than a preset reference value. If the level of the picture element signal is found to be lower than the reference value, the picture element signal will be stored in an image memory circuit 16 by a write circuit 15. The picture element signal thus stored is fed to a D/A conversion circuit 19 through a read circuit 18, where the digital signal is changed back into an analog picture signal which is then displayed on a television monitor 20. On the other hand, if the discriminating circuit 11 determines that the picture element signal level is higher than the preset reference value, the picture element signal will be fed to a light quantity adjusting circuit 12. The light quantity adjusting circuit 12 delivers a light quantity adjusting signal on the basis of the level of the picture element signal which was applied thereto. This light quantity adjusting signal is fed to the liquid crystal element 7 through a liquid crystal control circuit 13 and a driver 14.

The aforesaid image pick-up tube 6, discriminating circuit 11, light quantity adjusting circuit 12, liquid crystal control circuit 13, write circuit 15, read circuit 18, and television monitor 20 are controlled on the basis of a synchronizing signal from a synchronizing signal generating circuit 21, so that their operations are synchronous with each other. Further, the output from the liquid crystal control circuit 13 is fed to an arithmetic circuit 17. The arithmetic circuit 17 and the image memory circuit 16 are interconnected.

Figure 2:
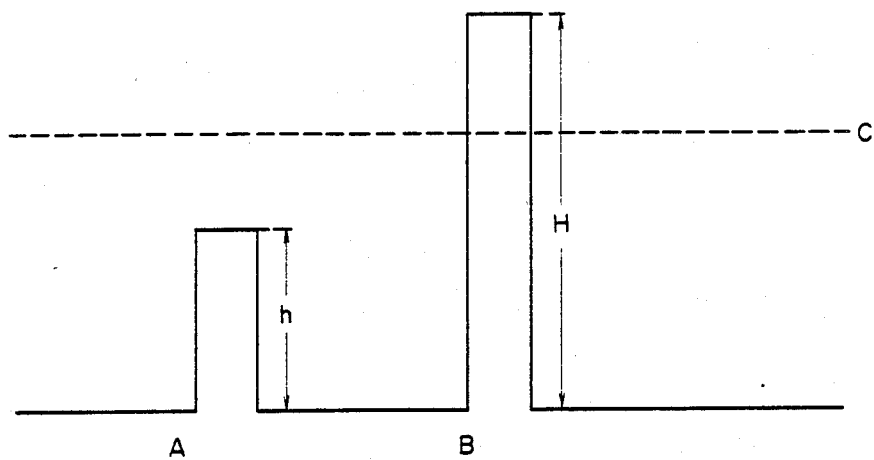
FIG. 2 is a diagram for explaining the discriminating operation in a discriminating circuit 11.
Figure 3:
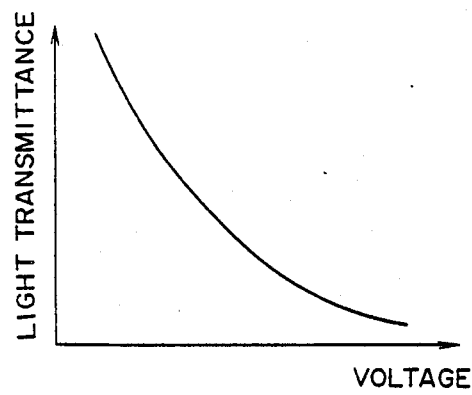
FIG. 3 is a graph showing the applied voltage versus light transmittance of a liquid crystal element 7.

FIG. 2 is a diagram for explaining the discriminating operation in the discriminating circuit 11. FIG. 3 is a graph showing the applied voltage versus light transmittance characteristic of the liquid crystal element 7. FIG. 4 is a view showing the state of the liquid crystal element 7 during correction.

The operation of the embodiment shown in FIG. 1 will now be described with reference to FIGS. 2 through 4. After the image of the organ 1 is magnified by the microscope 4, it is fed to the image pick-up tube 6 through the liquid crystal element 7 and optical fiber 8 and is thereby picked up. The output from the image pick-up tube 6 is fed to the amplifying circuit 9, where it is amplified to a suitable degree, whereupon it is fed to the A/D conversion circuit 10 which converts it into a digital picture element signal. The output from the A/D conversion circuit 10 is fed to the discriminating circuit 11. If the level of the applied picture element signal has a peak A below the preset reference C (see FIG. 2), the image is stored in the image memory circuit 16 via the write circuit 15. On the other hand, if the level of the applied picture element signal has a peak B above the reference level C, the picture element signal is fed to the light quantity adjusting circuit 12. The light quantity adjusting circuit 12 detects the level of the applied picture element signal and acts to increase the applied voltage on the corresponding region of the liquid crystal element 7 through the intermediary of the liquid crystal control circuit 13 and drive 14 so as to lower the level of the picture element signal, thereby lowering the light transmittance of that portion. For example, as shown in FIG. 4, if the image of the light source is on a region Z1 of the liquid crystal element 7, and if the level of the picture element signal for that portion is higher than the reference level C, then the voltage to be imposed on the region Z1 is raised to lower the light transmittance. Further, in the case where the image of the organ 1, which has an intricate uneven surface, is on the region Z2, if there is a portion therein whose brightness is higher than the reference value, the light transmittance of only that portion will be decreased. Thereby, it is possible to prevent seizure of the image pick-up tube 6.

In addition, if there is a need for information on the image prior to correction in image measurement, the level prior to correction of the portion where the level of the picture element signal was lowered by said correction is calculated, with the result being written on the portion of the image memory circuit 16 corresponding to the picture image. Thus, information on the image prior to correction can be obtained.

In addition, there are various types of liquid crystal elements 7 commercially available, but the more advantageous ones are those having electric field control double refraction effect and those having horizontal orientation type guest-host effect.

The above embodiment refers to a case where a microscope is equipped with an image pick-up tube, but the same effect can be expected also in cases where an endoscope is equipped with an image pick-up tube or where an eyeground camera is used.

Further, if an object to be photographed in a scene including a windowpane shadowed as by a building, the reflected light from the windowpane has heretofore made the amplification of the image signal impossible and also some portions of the image darker. This drawback, however, can be eliminated by applying this invention. Thus, this invention is useful for photography in general.

We claim:
1. An image pick-up device, comprising:
   a light source for irradiating an object;
   image pick-up means for picking up an image of said object;
   an optical system, disposed between said object and said image pick-up means for forming said image of said subject on said image pick-up means;
   designating means for designating a region of high brightness in said image of said object picked up by said image pick-up means;
   an image memory means for storing information representing said image of said object picked up by said image pick-up means;
   calculation means for calculating a brightness magnitude of said designated region of high brightness;
   writing means, receiving information representing said brightness magnitude from said calculating means, for writing said information into a portion of said image memory means corresponding to said designated region of high brightness; and
   light transmittance changing means connected with said optical system, for changing light transmittance in any desired region of said optical system and for decreasing light tansmittance in a region of said optical system corresponding to a said region of said image designated by said designating means as being a region of high brightness.

2. An image pick-up device as in claim 1, wherein said designating means includes means for comparing a brightness level of said image of said object, with a predetermined reference level for automatically designating a said region of high brightness.

3. An image pick-up device, comprising:
   a light source for irradiating an object;
   image pick-up means for picking up an image of said object;
   an optical system disposed between said object and said image pick-up means for forming said image of said object on said image pick-up means;
   designating means for designating a region of high brightness in said image of said object picked up by said image pick-up means;
   detecting means for detecting a brightness level of a said designated region of high brightness;
   image memory means for storing information representing said image of said object picked up by said image pick-up means;
   writing means, receiving information representing said brightness level from said detecting means, for writing said information into a portion of said image memory means corresponding to said designated region of high brightness; and
   light transmittance changing means receiving a representation of said detected brightness level of said designated region of high brightness from said detection means responsive to a designation of a region of high brightness by said designating means, for decreasing light transmittance in a region of said optical system corresponding to said designated region of high brightness in said image.

4. The image pick-up device as in claim 3, wherein said designating means includes means for comparing a brightness of said image of said object with a predetermined reference level to automatically designate a said region of high brightness.

* * * * *